US009103806B2

(12) United States Patent
Massaro

(10) Patent No.: US 9,103,806 B2
(45) Date of Patent: Aug. 11, 2015

(54) ROBOTIC SYSTEM WITH AUTONOMOUSLY OPERABLE TOOLS

(75) Inventor: Peter Massaro, Burlington, CT (US)

(73) Assignee: Protedyne Corporation, Windsor, CT (US)

( * ) Notice: Subject to any disclaimer, the term of this patent is extended or adjusted under 35 U.S.C. 154(b) by 1109 days.

(21) Appl. No.: 11/789,186

(22) Filed: Apr. 24, 2007

(65) Prior Publication Data

US 2008/0060719 A1 Mar. 13, 2008

Related U.S. Application Data

(60) Provisional application No. 60/794,356, filed on Apr. 24, 2006.

(51) Int. Cl.
| G01N 35/02 | (2006.01) |
| G01N 1/10 | (2006.01) |
| B65B 1/04 | (2006.01) |
| B65B 3/04 | (2006.01) |
| B67C 3/00 | (2006.01) |
| G01N 35/00 | (2006.01) |
| G01N 31/00 | (2006.01) |
| G01N 33/00 | (2006.01) |
| B01L 3/00 | (2006.01) |
| G01N 35/08 | (2006.01) |
| G01N 35/10 | (2006.01) |

(52) U.S. Cl.
CPC ........ *G01N 35/0099* (2013.01); *G01N 35/1074* (2013.01); *G01N 35/1009* (2013.01); *G01N 2035/00811* (2013.01)

(58) Field of Classification Search
USPC ............... 141/1, 11, 237; 436/47, 54, 180; 422/400, 63, 65, 66, 67
See application file for complete search history.

(56) References Cited

U.S. PATENT DOCUMENTS

| 5,660,792 | A | | 8/1997 | Koike | |
| 5,840,573 | A | * | 11/1998 | Fields | 435/287.2 |
| 6,045,755 | A | * | 4/2000 | Lebl et al. | 506/33 |
| 6,142,722 | A | * | 11/2000 | Genov et al. | 414/217 |

(Continued)

FOREIGN PATENT DOCUMENTS

| JP | 2001-523812 | 11/2001 |
| JP | 2005-521889 | 7/2005 |

(Continued)

OTHER PUBLICATIONS

International Search Report and Written Opinion PCT/US2007/010073 dated Oct. 26, 2007.

(Continued)

*Primary Examiner* — Jennifer Wecker
(74) *Attorney, Agent, or Firm* — Wolf, Greenfield & Sacks, P.C.

(57) ABSTRACT

Method and apparatus for performing a liquid handling process involves the use of a robotic device that manipulates a plurality of separate tools. A first tool may be removably engaged with the robotic device, which manipulates and control the first tool to perform at least one liquid handling task or operation with respect to at least one liquid sample. The first tool may then be positioned at a first location on a support, and disengaged from the robotic device. Thereafter, the first tool may perform at least one liquid handling task or operation while on the support and separated from the robotic device.

24 Claims, 1 Drawing Sheet

(56) References Cited

U.S. PATENT DOCUMENTS

| | | | |
|---|---|---|---|
| 6,491,491 B1 * | 12/2002 | Tsuneda et al. | 414/744.5 |
| 6,637,476 B2 * | 10/2003 | Massaro | 141/237 |
| 2002/0108857 A1 * | 8/2002 | Paschetto et al. | 204/457 |
| 2003/0183301 A1 * | 10/2003 | Massaro | 141/237 |
| 2004/0018119 A1 * | 1/2004 | Massaro | 422/100 |
| 2004/0028507 A1 * | 2/2004 | Massaro | 414/4 |
| 2005/0271551 A1 * | 12/2005 | Shumate et al. | 422/100 |
| 2005/0271552 A1 * | 12/2005 | Coassin et al. | 422/100 |
| 2006/0002824 A1 * | 1/2006 | Chang et al. | 422/100 |
| 2006/0016510 A1 * | 1/2006 | Porter et al. | 141/2 |
| 2006/0047363 A1 * | 3/2006 | Farrelly et al. | 700/245 |
| 2006/0087911 A1 * | 4/2006 | Herz et al. | 366/101 |
| 2006/0088447 A1 * | 4/2006 | Stimpson et al. | 422/100 |
| 2006/0156978 A1 * | 7/2006 | Lipson et al. | 118/708 |
| 2006/0160250 A1 * | 7/2006 | Bonassar et al. | 438/1 |
| 2008/0156117 A1 * | 7/2008 | Londo et al. | 73/864.14 |
| 2009/0298129 A1 * | 12/2009 | Spence et al. | 435/91.2 |

FOREIGN PATENT DOCUMENTS

| | | |
|---|---|---|
| JP | 2005-525816 | 9/2005 |
| WO | WO 99/25476 A2 | 5/1999 |
| WO | WO99/44068 A1 | 9/1999 |
| WO | WO02/059563 A | 8/2002 |
| WO | WO 03/085407 A1 | 10/2003 |
| WO | WO 03/097808 A2 | 9/2005 |
| WO | WO2005/124366 A | 12/2005 |
| WO | WO 2005124366 A1 * | 12/2005 |

OTHER PUBLICATIONS

English translation of the Decision of Rejection, issued May 8, 2012, for Japanese Patent Application No. 2009-507786 (2 pages).
English translation of the Reason for Rejection, issued Dec. 5, 2011, for Japanese Patent Application No. 2009-507786 (2 pages).
Communication under Rule 71(3) dated Jan. 25, 2013 for European Patent Application No. 07 776 215.1 (19 pages).

* cited by examiner

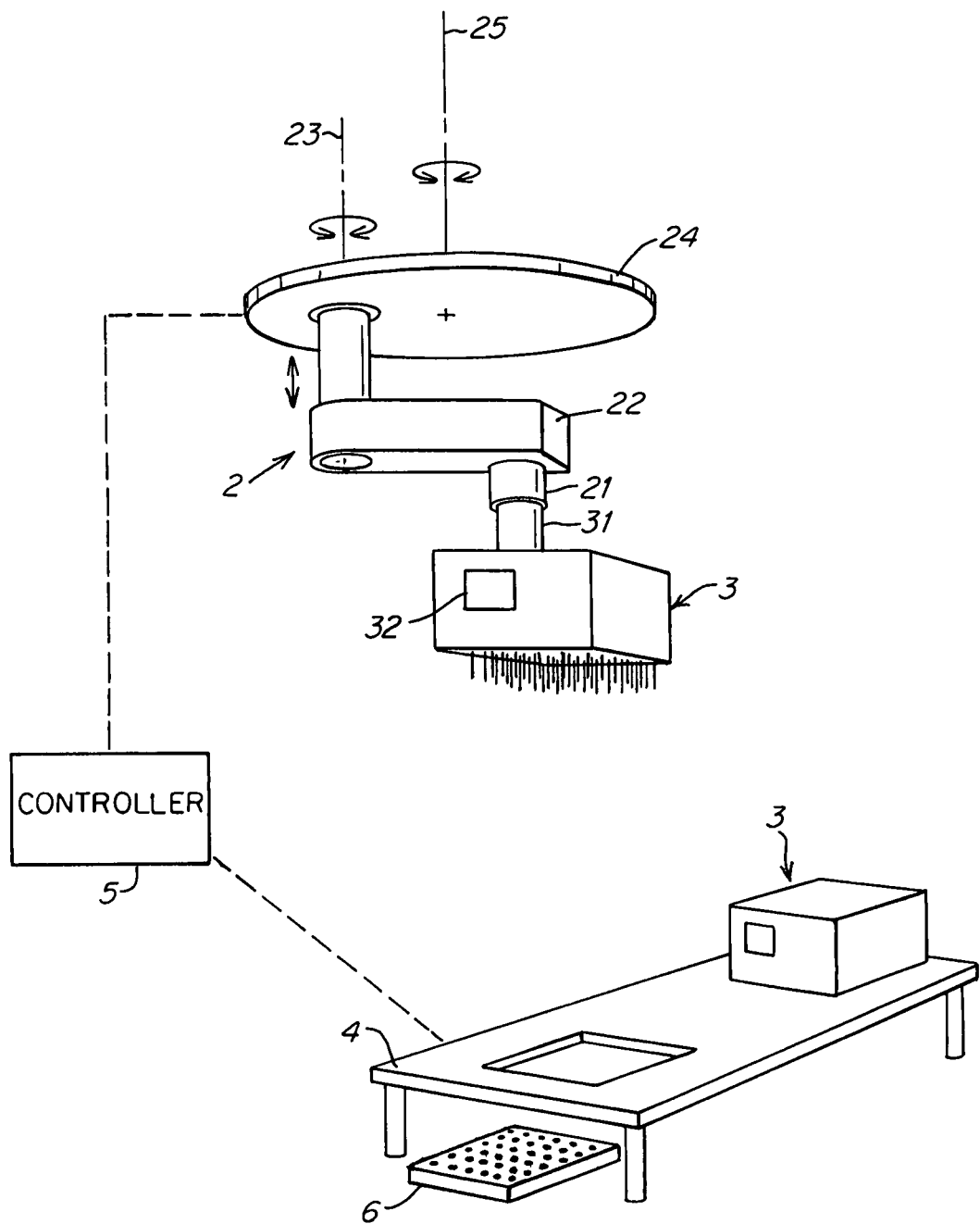

ROBOTIC SYSTEM WITH AUTONOMOUSLY OPERABLE TOOLS

This application claims priority to U.S. Provisional Application 60/794,356, filed Apr. 24, 2006, which is hereby incorporated by reference in its entirety.

BACKGROUND OF INVENTION

1. Field of the Invention

This invention relates to robotic systems with autonomously operable tools.

2. Related Art

Robotic systems are widely used for manipulating objects and performing other tasks. Such systems are commonly used, for example, in manipulating liquid samples involved in genomic and/or proteomic analysis and other processing. Some robotic systems adapted to handle liquid samples may use two or more removable pipetting heads or other sample handling tools. In some arrangements, a robotic arm may exchange two or more tools for one another, e.g., may use a gripping tool to move a multiwell plate, drop the gripping tool on a stand and pick up a second liquid handling tool on the stand for use with aspirating or dispensing samples in the multiwell plate.

SUMMARY OF INVENTION

The inventor has developed a method and apparatus for increasing the throughput of robotic systems that use interchangeable tools, e.g., two or more pipetting heads or other tools capable of performing liquid handling operations. In one aspect of the invention, a sample handling system may use a single robotic arm that is capable of removably engaging with (e.g., picking up/manipulating/controlling/dropping) multiple liquid handling tools. In one aspect of the invention, however, the tools may operate autonomously, e.g., when placed on a stand or other support separate from the robotic arm, to perform one or more liquid sample handling operations. That is, tools that are disconnected from the robotic arm may perform one or more liquid handling functions, e.g., with respect to one or more liquid samples located in a sample holder, such as a multiwell plate, vial(s), or other, or that are located in a channel or other area of the tool. One feature of this arrangement may be that liquid handling processing may be performed in parallel by multiple tool heads that are disconnected from, yet are capable of being manipulated by a single robotic arm. This may speed the liquid handling process and/or reduce the number of robotic arms (or arm movements) needed to perform an overall liquid handling process.

For example, a single robotic arm may be used to manipulate a plurality of pipetting heads to perform a magnetic bead separation process. (As is known in the art, magnetic beads are commonly used to separate desired genetic fragments from other fragments by attaching the desired fragments to primers or other segments on the magnetic beads, and then extracting the beads with the attached fragments.) To start the process, an initial step may include the robotic arm manipulating a pipetting head so as to pick up magnetic beads in multiple pipette tips or other channels on the tool. The beads may be contained in a liquid medium and have a desired primer or other compound secured to each bead, e.g., for use in a genetic separation process. Pick up of the magnetic beads may be performed at a central location, e.g., a tray holding the liquid medium and beads. Thereafter, the robotic arm may place the current pipetting head on a support, e.g., so that the head is associated with one or more multiwell plates or other liquid sample holders at the support location. The pipetting head may be disengaged from the robotic arm while on the support, freeing the robotic arm to perform other tasks, such as picking up a next pipetting head. However, each pipetting head that is placed on the support may continue to perform liquid handling tasks with respect to one or more liquid samples, e.g., in the pipette channels and/or in an associated multiwell plate, while on the support. The liquid sample handling tasks may include one or more of aspirating, dispensing, mixing, separating and/or other tasks, and may be performed by the tool without being connected to the robotic arm. This may be advantageous when certain processes of a protocol performed by the tool on a plurality of liquid samples take significant time and/or do not require connection of a tool to the robotic arm. Thus, the number of liquid samples, e.g., located in multiwell plates or other sample holders, that may be processed by the system may be limited only by the number of tools available to the robotic arm, and not necessarily by the amount of time it takes a single pipette head or other tool to perform a set of processes on a sample. It should be understood that liquid sample handling tasks performed in various aspects of the invention are not limited to those operations performed in a magnetic bead separation process, but instead may be related to any suitable process(es), e.g., a protein extraction process performed within reagent tips on a pipetting head or any other suitable process.

In one aspect of the invention, a method for performing a liquid handling process involves the use of a robotic device that manipulates a plurality of separate tools. A first tool is removably engaged with the robotic device, which is used to manipulate and control the first tool to perform at least one liquid handling task or operation with respect to at least one liquid sample. The robotic device is then used to position the first tool at a first location on a support, and the first tool is disengaged from the robotic device to leave the first tool at the first location on the support. The first tool is thereafter operated to perform at least one liquid handling task or operation while on the support. Thus, the first tool may perform a liquid handling operation both while connected and not connected to the robotic device. In one embodiment, the tool may perform liquid handling operations while on the support and without receiving control signals from a controller separate from the tool. Instead, the tool may perform the liquid handling operations under its own control. Power may or may not be supplied to the tool while it is located on the support.

In another aspect of the invention, a tool for use with a robotic device includes a plurality of channels each adapted to perform a liquid sample handling operation with respect to a liquid sample. A tool interface may receive power and/or control signals, and may include a coupling adapted to removably engage with a robotic device to allow the robotic device to manipulate the tool. The tool may also have a tool controller that controls operation of the plurality of channels, e.g., by controlling one or more portions of the tool to move so as to cause fluid flow in the channels. The tool may be adapted to perform a liquid sample handling operation when engaged with the robotic device at the coupling, as well as to perform a liquid sample handling operation when placed on a support separate from the robotic device.

In another aspect of the invention, a system for performing liquid handling processes on a plurality of liquid samples includes a robotic device adapted to manipulate a tool in a work area and that includes a coupling for removably engaging with the tool. A support, which is separate from the robotic device, is provided to engage with at least one tool when the tool is disengaged from the robotic device. A plurality of tools may be provided for use with the robotic device, with each tool including a plurality of channels each adapted to perform a liquid sample handling operation with respect to a liquid sample. The tools may also include an interface that receives power and/or control signals, and that includes a coupling adapted to removably engage with the robotic device to allow the robotic device to manipulate the tool. A controller on each tool may control operation of the plurality of channels, so that the tool is adapted to perform a liquid sample handling operation when engaged with the robotic device at the coupling, and to perform a liquid sample handling operation when placed on the support.

These and other aspects of the invention will be apparent from the following description and claims.

BRIEF DESCRIPTION OF THE DRAWINGS

Aspects of the invention are described with reference to the following drawings in which numerals reference-like elements, and wherein:

FIG. 1 is a perspective view of a liquid handling system having at least one robotic arm and a plurality of liquid handling tools in accordance with aspects of the invention.

DETAILED DESCRIPTION

This invention is not limited in its applications to the details of construction and the arrangement of components set forth in the following description or illustrated in the drawings. The invention is capable of other embodiments and of being practiced or of being carried out in various ways. For example, illustrative embodiments of the invention are described below with reference to use in a liquid handling environment. However, it should be understood that aspects of the invention may be used in robotic systems for any suitable application.

FIG. 1 shows an illustrative embodiment of a liquid sample handling system 1 that includes a robotic device 2. The robotic device 2 may include a Cartesian robot, SCARA-type robot, and/or any other type of robot having any suitable number of degrees of freedom. In this illustrative embodiment, the robotic device 2 is a SCARA-type robot (like that described in U.S. application Ser. No. 11/339,036, filed Jan. 25, 2006, which is hereby incorporated by reference in its entirety) which includes an arm 22 that may be rotated about an axis 23 and moved linearly along the axis 23 relative to a turntable 24, which may itself be rotated about an axis 25. The robotic device 2 may be adapted to pick up and drop two or more tools 3 with respect to a support 4, such as a gripping tool (e.g., for picking and placing multiwell plates or other sample holders), tools for performing optical or other analysis of liquid samples in sample holders, and/or tools for performing other liquid sample handling tasks or operations. The robotic device 2 may include a coupling 21 that allows the device 2 to removably engage with a tool 3, which may itself have a corresponding coupling 31. The couplings 21 and 31 may allow for mechanical engagement between the robotic device 2 and the tool 3 as well as provide electrical, optical, pneumatic, hydraulic and/or other connections to provide power and/or control signals to the tool 3. Power and/or control signals provided to the tool 3 may be generated by a system controller 5, which may also function to control operation of the robotic device 2 and/or other portions of the system 1. Control signals provided to the tool 3 may be in any form, and may be acted on by the tool 3 in any way. For example, the system controller 5 may provide low level control signals to the tool 3 that define explicit control instructions. Alternately, or in addition, the system controller 5 may provide higher level instructions to a tool controller 32 on the tool 3, which may decode the high level instructions, and generate lower level control signals for one or more portions of the tool 3 to perform the function(s) called for by the system controller 5. In one embodiment, the tool controller 32 may store instructions provided by the system controller 5, and use the stored instructions for later liquid sample handling operations performed while disconnected from the robotic device 2. For example, the system controller 5 may provide instructions to the tool controller 32 to perform one or more tasks with respect to liquid samples held by the tool 3 once the tool 3 is disconnected from the robotic device 2. The tools 3 may also send information to the system controller 5, e.g., regarding position feedback, the processing status of an associated liquid sample or set of samples and/or other information. Communication between the tools 3 and system controller 5 may be via wired and/or wireless connection, e.g., tools 3 may communicate wirelessly with the system controller 5 while disconnected from the robotic device 2 and on the support 4.

The support 4 may be arranged in any suitable way for engaging with one or more tools 3. In this illustrative embodiment, the support 4 is shown as a table-shaped arrangement with openings provided to allow a portion of a tool to extend below the support 4 and toward a sample holder 6. However, it should be understood that the support 4 may be arranged in any other suitable way. For example, tools 3 may be placed on or under a flat, horizontal surface with no openings that serves as a support 4. Alternately, the support 4 may include a vertical surface to which tools 3 are engaged. In other embodiments, the support 4 may include a frame, one or more bars, rods, and/or other structures that engage with a tool 3. In short, the support 4 may have any suitable arrangement.

While connected to the support 4, two or more of the tools 3 may receive power (electrical, pneumatic, or other) and/or control signals (electrical, pneumatic or other) via a connection with the support 4. The connection between the tools 3 and the support 4 may be established using the same connection interface as that used between the robot device 2 and the tools 3 when the tool is attached to the robot device 2 (e.g., the coupling 31), or may be established using a separate connection arrangement that is part of the tool interface. Thus, the tools 3 may perform one or more liquid sample handling tasks while mounted on the support 4 and disconnected from the robotic device 2. While on the support 4, a tool 3 may be associated with one or more sample holders 6, such as a multiwell plate or other, and sample handling tasks may be performed by the tool 3 with respect to the sample holder(s) 6. As discussed above, the tools 3 may perform sample handling tasks while on the support 4 using stored control instructions and/or based on real-time instructions received from the system controller 5. Tools 3 may also send information to the system controller 5, e.g., indicating a current task being performed, a sample processing status, etc. Some of the liquid handling tasks that may be performed by the tools 3 include, aspiration, dispensing, mixing, sample analysis, extending a pipette tip or other channel toward and away from wells in a sample holder 6 and others. The tools 3 may have multiple pipette tips or other channels that may each operate with respect to a well in a multiwell plate or other sample holder arrangement. Each of the pipette tips or other channels may be individually controlled by the tool 3 to perform specific tasks. Thus, one pipette tip, capillary tube or other channel on a tool 3 may be individually controlled to aspirate or dispense with respect to a corresponding well in a multiwell plate or other sample holder 6. Alternately, multiple tips or other channels may be controlled to work together in performing liquid sample handling tasks.

In some cases, tools 3 may be capable of performing multiple different tasks, such as gripping and liquid sample handling operations, or any other suitable combination. As used herein, a liquid sample handling task or operation includes at least aspirating a liquid sample, dispensing a liquid sample, agitating a liquid sample in a channel of the tool, mixing two substances together at a channel of the tool, performing an analysis of a liquid sample and/or separating components of a liquid sample. If a tool 3 performs operations with respect to multiple sample holders 6, the sample holders 6 may be moved with respect to the tool 3 when on the support 4, e.g., by a conveyor belt, by the robotic device 2 or other arrangement. Alternately, tools 3 may be moved with respect to sample holders 6, e.g., there may be several different supports 4 and/or tools 3 may be moved to different locations on a single support 4 to perform liquid sample handling operations.

With the above arrangement and similar configurations, the robotic device 2 and system controller 5 may multiplex the tools 3 in such a way that use of the robotic device 2 is efficient and so that, whenever possible, processing of samples in multiple well plates or other sample holders is performed by multiple tools 3 while the tools are disconnected from the robotic device 2. This arrangement may also allow the system 1 to move tools 3 on the support 4 and allow the tools 3 to process one or more sample holders 6 without having to move the sample holders 6. Thus, the system 1 may use different tools 3 to perform different processes on the sample holders 6, e.g., where the tools 3 are each specially configured to perform a particular process. Alternately, sample holders 6 may be moved with respect to tools 3 that may remain stationary on the support 4. For example, sample holders 6 may be moved by a conveyor, by the robot 2 or other arrangement relative to tools 3 mounted to the support 4. Tools may be swapped out from the support 4 as desired, e.g., one tool may be removed from the support 4 at a processing location and moved to a cleaning location on the support 4 so that pipette tips or other channels may be cleaned on the tool to ready the tool 3 for subsequent use. While the tool 3 is being cleaned, it may be replaced at the processing location by another tool 3 that has already completed cleaning and is ready for use.

In one illustrative embodiment, the system 1 may be used to perform a magnetic bead separation process with respect to liquid samples held by several multiwell plates. The robotic device 2 may have several tools 3 at its disposal, and may pick up each tool 3 so as to allow the tool to aspirate magnetic beads (in a liquid solution) or other material from a central storage tray. Thereafter, the robotic device 2 may place each tool 3 on the support 4, and the tool 3 may perform one or more tasks with respect to a set of one or more multiwell plates 6 at the support 4. For example, the tool 3 may aspirate liquid samples (containing genetic fragments) from one or more wells in a plate 6 so as to mix the samples from the plate with magnetic beads aspirated earlier. The genetic fragments and magnetic beads may be mixed, e.g., by repeatedly aspirating and/or dispensing from channels in the tool 3. Such processing may take time, e.g., while the beads are mixed with liquid samples and desired nucleic acid fragments are allowed to attach to the beads. Thus, the tools 3 may be disconnected from the device 2 while on the support 4 and allowed to perform their liquid sample handling tasks while the device 2 performs other tasks, such as preparing other tools 3 for similar processing. When the tool 3 is finished processing the multiwell plate(s), the robotic device 2 may pick up the tool 3 and use it in processing of other plates, and/or may remove the multiwell plate(s) and provide other plates for processing by the tool 3.

Other processing operations performed by tools 3 while on a support 4 will occur to those of skill in the art. For example, a tool 3 may be manipulated by a robotic device 2 so as to aspirate liquid samples from a first multiwell plate. Thereafter, the tool 3 may be placed on the support 4, and the tool 3 may dispense portions of the aspirated samples into wells one or more multiwell plates, e.g., to combine the aspirated samples with materials in the other multiwell plates prior to performing a PCR or other process on the plates.

The system controller 5 and/or the tool controller 32 may include any suitable devices and/or other components to perform the desired input/output and/or other functions. For example, the controller(s) may include any suitable programmable computing device, such as a general purpose computer, network of computers, microprocessor, and/or other data processing device. The controller(s) may also include any suitable volatile and/or non-volatile memory, communications devices, lines and/or interfaces, motors, drives, switches, relays, sensors or other feedback devices, and/or other components, as desired. The controller(s) may be implemented, at least in part, using any suitable software or other instructions that, when executed by a computing device, cause the controller(s) to perform desired functions. The controller(s) may include suitable user interfaces, such as a display, push buttons, graphical user interface, keyboards and/or other input devices, and so on.

Having described several aspects of this invention, it should be appreciated that various alterations, modifications and improvements will occur to those of skill in the art. Such alterations, modifications and improvements are intended to be part of this disclosure and are intended to be within the spirit and scope of the invention. Thus, the description and drawings herein are intended to be illustrative, not limiting.

The invention claimed is:

1. A method for performing a liquid handling process that involves the use of a robotic arm that manipulates a plurality of separate tools, the method comprising:
   removably engaging a first tool with the robotic arm;
   using the robotic arm to manipulate and to send control signals directly to the first tool to perform a first liquid handling operation while the first tool is engaged with the robotic arm, wherein the first liquid handling operation is performed with respect to a liquid sample and a sample holder, the sample holder being located off the robotic arm;
   using the robotic arm to position the first tool at a first location on a support;
   disengaging the first tool from the robotic arm to leave the first tool at the first location on the support; and
   operating the first tool to perform a second liquid handling operation while the first tool is disengaged from the robotic arm and on the support.

2. The method of claim 1, wherein the first tool includes a plurality of pipette channels, and the second liquid handling operation performed by the first tool on the support includes causing fluid flow in at least one of the plurality of pipette channels.

3. The method of claim 1, wherein the first tool includes a plurality of pipette channels, and the first liquid handling operation performed by the first tool when engaged with the robotic arm includes causing fluid flow in at least one of the plurality of pipette channels.

4. The method of claim 1, wherein the first tool includes a plurality of pipette channels arranged to interact with wells in a multiwell plate.

5. The method of claim 1, wherein the robotic arm is a SCARA robot.

6. The method of claim 1, further comprising a second tool adapted to perform at least one liquid handling operation with respect to at least one liquid sample, the method further comprising:
using the robotic arm to manipulate and control the second tool to perform at least one liquid handling operation with respect to at least one liquid sample while the second tool is engaged with the robotic arm and while the first tool performs at least one liquid handling operation while on the support.

7. The method of claim 1, wherein the first tool receives power and/or control signals while on the support.

8. The method of claim 1, wherein the first liquid handling operation includes aspirating a liquid sample, dispensing a liquid sample, agitating a liquid sample in a channel of the first tool, mixing two substances together at a channel of the first tool, performing an analysis of a liquid sample and/or separating components of a liquid sample.

9. The method of claim 1, wherein the first tool performs at least one liquid handling operation while on the support without receiving control signals from a system controller.

10. The method of claim 1, wherein the second liquid handling operation performed by the first tool while disengaged from the robotic arm and on the support is performed with respect to a liquid sample that includes at least one magnetic bead.

11. The method of claim 1, wherein the step of removably engaging a first tool with the robotic arm includes:
engaging a coupling of the robotic arm with a tool interface on the first tool.

12. The method of claim 11, further comprising:
providing power and/or control signals to the first tool via the tool interface.

13. The method of claim 11, wherein the step of using the robotic arm to manipulate and control the first tool comprises:
manipulating the first tool via the engaged coupling and tool interface.

14. The method of claim 11, wherein the engagement of the coupling with the tool interface provides a mechanical engagement of the robotic arm with the first tool.

15. The method of claim 14, wherein the engagement of the coupling with the tool interface provides a connection for providing power and/or control signals from the robotic arm to the first tool.

16. The method of claim 1, wherein the first tool includes a tool controller that controls operation of the first tool.

17. The method of claim 1, wherein the step of operating the first tool to perform the second liquid handling operation while disengaged from the robotic arm and on the support comprises:
using instructions stored by a tool controller that is part of the first tool to perform second liquid handling operation while disengaged from the robotic arm and on the support.

18. The method of claim 17, further comprising:
providing the stored instructions from the robotic system to the first tool while the first tool is engaged with the robotic arm; and
storing the stored instructions at the tool controller for later use while the first tool is disengaged from the robotic arm and on the support.

19. The method of claim 1, wherein the step of operating the first tool to perform the second liquid handling operation while disengaged from the robotic arm and on the support comprises:
cleaning one or more pipette tips or other channels of the first tool.

20. The method of claim 1, further comprising:
sending information from the first tool to a system controller regarding a status of the second liquid handling operation performed while the first tool is disengaged from the robotic arm and on the support.

21. A method for performing a liquid handling process that involves the use of a robotic arm that manipulates a plurality of separate tools, the method comprising:
removably engaging a first tool with the robotic arm;
using the robotic arm to manipulate and to send control signals directly to the first tool to perform a first liquid handling operation while the first tool is engaged with the robotic arm, wherein the first liquid handling operation is performed with respect to a liquid sample and a sample holder, the sample holder being located off the robotic arm;
providing instructions to the first tool while the first tool is engaged with the robotic arm;
storing the instructions at a tool controller that is part of the first tool;
using the robotic arm to position the first tool at a first location on a support;
disengaging the first tool from the robotic arm to leave the first tool at the first location on the support; and
operating the first tool to perform a second liquid handling operation according to the stored instructions while the tool is disengaged from the robotic arm and on the support.

22. A method for performing a liquid handling process that involves the use of a robotic arm that manipulates a plurality of separate tools, the method comprising:
removably engaging a first tool with the robotic arm;
using the robotic arm to manipulate and to send control signals directly to the first tool to perform a first liquid handling operation while the first tool is engaged with the robotic arm, wherein the first liquid handling operation is performed with respect to a liquid sample and a sample holder, the sample holder being located off the robotic arm;
using the robotic arm to position the first tool at a first location on a support;
disengaging the first tool from the robotic arm to leave the first tool at the first location on the support;
operating the first tool to perform a second liquid handling operation with a first sample holder while the first tool is disengaged from the robotic arm and on the support; and
advancing the first sample holder away from the first tool, then advancing a second sample holder toward the first tool for use by the first tool while the first tool is on the support.

23. The method of claim 22, wherein the step of advancing the first sample holder away from the first tool, then advancing the second sample holder toward the first tool is performed by a conveyor belt.

24. The method of claim 1, wherein, according to instructions received from a system controller, the first tool performs at least one liquid handling operation while engaged with the robotic arm and at least one liquid handling operation while disengaged from the robotic arm and on the support.

* * * * *